(12) United States Patent
Dolev et al.

(10) Patent No.: US 10,485,470 B2
(45) Date of Patent: *Nov. 26, 2019

(54) EARLY DIAGNOSIS AND TREATMENT OF ALZHEIMER DISEASE AND MILD COGNITIVE IMPAIRMENT

(71) Applicant: QUANTALX NEUROSCIENCE LTD, Zur Moshe (IL)

(72) Inventors: Iftach Dolev, Zur Moshe (IL); Hilla Fogel, Beit Dagan (IL)

(73) Assignee: QUANTALX NEUROSCIENCE LTD, Beit Dagan (IL)

( * ) Notice: Subject to any disclaimer, the term of this patent is extended or adjusted under 35 U.S.C. 154(b) by 0 days.

This patent is subject to a terminal disclaimer.

(21) Appl. No.: 15/547,502

(22) PCT Filed: Feb. 3, 2016

(86) PCT No.: PCT/IL2016/050124
§ 371 (c)(1),
(2) Date: Jul. 30, 2017

(87) PCT Pub. No.: WO2016/125159
PCT Pub. Date: Aug. 11, 2016

(65) Prior Publication Data
US 2018/0014772 A1    Jan. 18, 2018

Related U.S. Application Data

(60) Provisional application No. 62/111,122, filed on Feb. 3, 2015, provisional application No. 62/111,123, filed on Feb. 3, 2015.

(51) Int. Cl.
*A61B 5/00* (2006.01)
*A61N 2/00* (2006.01)
(Continued)

(52) U.S. Cl.
CPC .......... *A61B 5/4088* (2013.01); *A61B 5/0476* (2013.01); *A61B 5/0484* (2013.01);
(Continued)

(58) Field of Classification Search
CPC .. A61N 1/36017; A61N 1/20; A61N 1/36031; A61N 1/36025; A61N 1/0456;
(Continued)

(56) References Cited

U.S. PATENT DOCUMENTS 5,263,481 A    11/1993 Axelgaard
5,833,622 A    11/1998 Meathrel et al.
(Continued)

FOREIGN PATENT DOCUMENTS

EP    1008365 A1    6/2000
WO    WO2009/044271    *    4/2009
(Continued)

OTHER PUBLICATIONS

Alschuler et al. "Identifying electrode bridging from electrical distance distributions: a survey of publicly-available EEG data using a new method" Clinical Neurophysiology. Mar. 1, 2014;125(3):484-90.
(Continued)

*Primary Examiner* — Christopher Koharski
*Assistant Examiner* — Roland Dinga
(74) *Attorney, Agent, or Firm* — Mark S. Cohen; Pearl Cohen Zedek Latzer Baratz LLP (57) ABSTRACT

Methods, systems and devices for detecting and treating cognitive impairment conditions by inducing stimulation to a predetermined region of the brain and measuring neural activity response to the stimulation and evaluating a neuroplasticity of neural-structures in a predetermined brain
(Continued)

region, then stimulating the predetermined brain region to treat the cognitive impairment condition.

18 Claims, 8 Drawing Sheets

(51) Int. Cl.
| | |
|---|---|
| *A61B 5/0476* | (2006.01) |
| *A61N 1/36* | (2006.01) |
| *A61N 1/04* | (2006.01) |
| *A61B 5/0484* | (2006.01) |
| *A61M 21/00* | (2006.01) |
| *A61N 1/20* | (2006.01) |
| *A61N 2/02* | (2006.01) |
| *A61N 1/05* | (2006.01) |
| *A61B 5/04* | (2006.01) |

(52) U.S. Cl.
CPC .......... *A61B 5/4076* (2013.01); *A61B 5/4836* (2013.01); *A61B 5/4848* (2013.01); *A61M 21/00* (2013.01); *A61N 1/0456* (2013.01); *A61N 1/20* (2013.01); *A61N 1/36017* (2013.01); *A61N 1/36025* (2013.01); *A61N 1/36031* (2017.08); *A61N 2/006* (2013.01); *A61B 5/04012* (2013.01); *A61B 5/4094* (2013.01); *A61M 2021/005* (2013.01); *A61M 2021/0027* (2013.01); *A61N 1/0529* (2013.01); *A61N 2/02* (2013.01)

(58) Field of Classification Search
CPC ........ A61N 1/0529; A61N 2/006; A61N 2/02; A61M 2021/0027; A61M 2021/005; A61M 21/00
See application file for complete search history.

(56) References Cited

U.S. PATENT DOCUMENTS

| | | |
|---|---|---|
| 8,457,731 B2 | 6/2013 | Tonini |
| 2002/0095080 A1 | 7/2002 | Cory et al. |
| 2002/0188330 A1 | 12/2002 | Gielen et al. |
| 2004/0219153 A1 | 11/2004 | Gehlsen |
| 2006/0258788 A1 | 11/2006 | Coggins et al. |
| 2008/0294031 A1 | 11/2008 | Wilson et al. |
| 2009/0105576 A1 | 4/2009 | Do et al. |
| 2009/0198305 A1 | 8/2009 | Naroditsky et al. |
| 2010/0298623 A1 | 11/2010 | Mishelevich |
| 2010/0324441 A1 | 12/2010 | Hargrove et al. |
| 2011/0118536 A1 | 5/2011 | Phillips |
| 2011/0118661 A1 | 5/2011 | Pless |
| 2011/0207988 A1 | 8/2011 | Ruohonen |
| 2011/0224571 A1 | 9/2011 | Pascual-leone |
| 2011/0319975 A1 | 12/2011 | Johnson et al. |
| 2012/0101366 A1 | 4/2012 | Ruohonen et al. |
| 2013/0267763 A1 | 10/2013 | Schneider |
| 2013/0281759 A1 | 10/2013 | Hagedorn et al. |
| 2014/0058189 A1 | 2/2014 | Stubbeman |
| 2014/0276184 A1 | 9/2014 | Neuvonen |

FOREIGN PATENT DOCUMENTS

| | | |
|---|---|---|
| WO | WO/2009/044271 | 4/2009 |
| WO | WO 2015/034981 A1 | 3/2015 |

OTHER PUBLICATIONS

Anand et al. "Transcranial magnetic stimulation: neurophysiological applications and safety" Brain and cognition. Dec. 1, 2002;50(3):366-86.
Apkarian et al. "Towards a theory of chronic pain" Progress in neurobiology. Feb. 1, 2009;87(2):81-97.
Arul-Anandam et al. "Transcranial direct current stimulation: a new tool for the treatment of depression?" Journal of affective disorders. Oct. 1, 2009;117(3):137-45.
Bolognini et al. "Motor and parietal cortex stimulation for phantom limb pain and sensations" Pain®. Aug. 1, 2013;154(8):1274-80.
Brown et al. "Motor cortex stimulation for central and neuropathic pain: current status" Pain. Aug. 1, 2003;104(3):431-5.
Eisenberg et al. "Evidence for cortical hyperexcitability of the affected limb representation area in CRPS: a psychophysical and transcranial magnetic stimulation study" Pain. Jan. 1, 2005;113(1-2):99-105.
Eto et al. "Inter-regional contribution of enhanced activity of the primary somatosensory cortex to the anterior cingulate cortex accelerates chronic pain behavior" Journal of Neuroscience. May 25, 2011;31(21):7631-6.
Flor H. "Phantom-limb pain: characteristics, causes, and treatment" The Lancet Neurology. Jul. 1, 2002;1(3):182-9.
Flor et al. "Extensive reorganization of primary somatosensory cortex in chronic back pain patients" Neuroscience letters. Mar. 7, 1997;224(1):5-8.
Freitas et al. "Assessing brain plasticity across the lifespan with transcranial magnetic stimulation: why, how, and what is the ultimate goal?" Frontiers in neuroscience. Apr. 2, 2013;7:42.
Gandiga et al. "Transcranial DC stimulation (tDCS): a tool for double-blind sham-controlled clinical studies in brain stimulation" Clinical neurophysiology. Apr. 1, 2006;117(4):845-50.
Giesbrecht et al. "A comparison of pressure pain detection thresholds in people with chronic low back pain and volunteers without pain" Physical therapy. Oct. 1, 2005;85(10):1085-92.
Giesecke et al. "Evidence of augmented central pain processing in idiopathic chronic low back pain" Arthritis & Rheumatism: Official Journal of the American College of Rheumatology. Feb. 2004;50(2):613-23.
International Search Report for PCT Application No. PCT/IL2017/050160 dated Jun. 4, 2017.
Islam et al. "Increase in the calcium level following anodal polarization in the rat brain" Brain research. Jul. 3, 1995;684(2):206-8.
Jacobs et al. "Low back pain associates with altered activity of the cerebral cortex prior to arm movements that require postural adjustment" Clinical Neurophysiology. Mar. 1, 2010;121(3):431-40.
Janicak et al. "Transcranial magnetic stimulation in the treatment of major depressive disorder: a comprehensive summary of safety experience from acute exposure, extended exposure, and during reintroduction treatment" Journal of Clinical Psychiatry, Feb. 1, 2008;69(2):222-32.
Jensen et al. "New insights into neuromodulatory approaches for the treatment of pain" The journal of Pain. Mar. 1, 2008;9(3):193-9.
Khedr et al. "Longlasting antalgic effects of daily sessions of repetitive transcranial magnetic stimulation in central and peripheral neuropathic pain" Journal of Neurology, Neurosurgery & Psychiatry. Jun. 1, 2005;76(6):833-8.
Khedr et al. "Therapeutic trial of repetitive transcranial magnetic stimulation after acute ischemic stroke" Neurology. Aug. 9, 2005;65(3):466-8.
Kim et al. "Rapid synaptic remodeling in the adult somatosensory cortex following peripheral nerve injury and its association with neuropathic pain" Journal of Neuroscience. Apr. 6, 2011;31(14):5477-82.
Larkin et al. "Novel therapies in AML: reason for hope or just hype" Am Soc Clin Oncol Educ Book. 2014;2014:e341-51.
Lauro et al. "TDCS increases cortical excitability: Direct evidence from TMS-EEG" Cortex. Sep. 1, 2014;58:99-111.
Lefaucheur et al. "Neurogenic pain relief by repetitive transcranial magnetic cortical stimulation depends on the origin and the site of pain" Journal of Neurology, Neurosurgery & Psychiatry. Apr. 1, 2004;75(4):612-6.
Lichtenegger et al. "Current strategies in immunotherapy for acute myeloid leukemia" Immunotherapy. Jan. 2013;5(1):63-78.
Liebetanz et al. "Anticonvulsant effects of transcranial direct-current stimulation (tDCS) in the rat cortical ramp model of focal epilepsy" Epilepsia. Jul. 2006;47(7):1216-24.

(56) References Cited

OTHER PUBLICATIONS

Lloyd et al. "Differences in low back pain behavior are reflected in the cerebral response to tactile stimulation of the lower back" Spine. May 20, 2008;33(12):1372-7.
Machii et al. "Safety of rTMS to non-motor cortical areas in healthy participants and patients" Clinical Neurophysiology. Feb. 1, 2006;117(2):455-71.
Martner et al. "Immunotherapeutic strategies for relapse control in acute myeloid leukemia" Blood reviews. Sep. 1, 2013;27(5):209-16.
McNickle et al. "Paired associative transcranial alternating current stimulation increases the excitability of corticospinal projections in humans" The Journal of physiology, Apr. 2015;593(7):1649-66.
Mhalla et al. "Alteration of cortical excitability in patients with fibromyalgia" Pain. Jun. 1, 2010;149(3):495-500.
Moriwaki A. "Polarizing currents increase noradrenaline-elicited accumulation of cyclic AMP in rat cerebral cortex" Brain research. Mar. 29, 1991;544(2):248-52.
Moseley GL. "A pain neuromatrix approach to patients with chronic pain" Manual therapy. Aug. 1, 2003;8(3):130-40.
Nikulin et al. "Modulation of electroencephalographic responses to transcranial magnetic stimulation: evidence for changes in cortical excitability related to movement" European Journal of Neuroscience. Sep. 2003;18(5):1206-12.
Nitsche et al. "Excitability changes induced in the human motor cortex by weak transcranial direct current stimulation" The Journal of physiology. Sep. 1, 2000;527(3):633-9.
Nitsche et al. "Modulation of cortical excitability by weak direct current stimulation—technical, safety and functional aspects" In Supplements to Clinical neurophysiology Jan. 1, 2003 (vol. 56, pp. 255-276). Elsevier.
Nitsche et al. "Facilitation of implicit motor learning by weak transcranial direct current stimulation of the primary motor cortex in the human" Journal of cognitive neuroscience. May 15, 2003;15(4):619-26.
Nitsche et al. "Level of action of cathodal DC polarisation induced inhibition of the human motor cortex" Clinical Neurophysiology. Apr. 1, 2003;114(4):600-4.
Nitsche et al. "MRI study of human brain exposed to weak direct current stimulation of the frontal cortex" Clinical Neurophysiology. Oct. 1, 2004;115(10):2419-23.
Nitsche et al. "Transcranial direct current stimulation: state of the art 2008" Brain stimulation. Jul. 1, 2008;1(3):206-23.
Nuti et al. "Motor cortex stimulation for refractory neuropathic pain: four year outcome and predictors of efficacy" Pain. Nov. 1, 2005;118(1-2):43-52.
O'Connel et al. "Transcranial direct current stimulation of the motor cortex in the treatment of chronic nonspecific low back pain: a randomized, double-blind exploratory study" The Clinical journal of pain. Jan. 1, 2013;29(1):26-34.
O'Reardon et al, "Efficacy and safety of transcranial magnetic stimulation in the acute treatment of major depression: a multisite randomized controlled trial" Biological psychiatry. Dec. 1, 2007;62(11):1208-16.
Pascual-Leone et al. "Transcranial magnetic stimulation and neuroplasticity" Neuropsychologia. Nov. 1, 1998;37(2):207-17.
Pascual-Marqui et al. "Low resolution brain electromagnetic tomography (LORETA) functional imaging in acute, neuroleptic-naive, first-episode, productive schizophrenia" Psychiatry Research: Neuroimaging. Jun. 30, 1999;90(3):169-79.
Paulus W. "Transcranial brain stimulation: potential and limitations" e-Neuroforum. Sep. 1, 2014;5(2):29-36.
Pellicciari et al. "Excitability modulation of the motor system induced by transcranial direct current stimulation: a multimodal approach. Neuroimage" Dec. 1, 2013;83:569-80.
Poreisz et al. "Safety aspects of transcranial direct current stimulation concerning healthy subjects and patients" Brain research bulletin. May 30, 2007;72(4-6):208-14.
Rogasch et al. "Assessing cortical network properties using TMS-EEG" Human brain mapping. Jul. 2013;34(7):1652-69.
Rossi et al. "Safety of TMS Consensus Group. Safety, ethical considerations, and application guidelines for the use of transcranial magnetic stimulation in clinical practice and research" Clinical neurophysiology. Dec. 1, 2009;120(12):2008-39.
Sauseng et al. "Spontaneous locally restricted EEG alpha activity determines cortical excitability in the motor cortex" Neuropsychologia. Jan. 1, 2009;47(1):284-8.
Schestatsky et al. "Simultaneous EEG monitoring during transcranial direct current stimulation" Journal of visualized experiments: JoVE. 2013(76).
Sung et al. "Efficacy of coupling inhibitory and facilitatory repetitive transcranial magnetic stimulation to enhance motor recovery in hemiplegic stroke patients" Stroke, May 1, 2013;44(5):1375-82.
Supplementary European Search Report for Euorpean application No. 16746238 dated Jan. 23, 2018.
Theodore WH. "Transcranial magnetic stimulation in epilepsy" Epilepsy currents. Nov. 2003;3(6):191-7.
Töpper et al. "Repetitive transcranial magnetic stimulation of the parietal cortex transiently ameliorates phantom limb pain-like syndrome" Clinical Neurophysiology. Aug. 1, 2003;114(8):1521-30.
Tsao et al. "Persistence of improvements in postural strategies following motor control training in people with recurrent low back pain" Journal of electromyography and kinesiology. Aug. 1, 2008;18(4):559-67.
Tsubokawa et al. "Treatment of thalamic pain by chronic motor cortex stimulation" Pacing and Clinical Electrophysiology. Jan. 1, 1991;14(1):131-4.
Vartiainen et al. "Cortical reorganization in primary somatosensory cortex in patients with unilateral chronic pain" The journal of pain. Aug. 1, 2009;10(8):854-9.
Wassermann EM. "Risk and safety of repetitive transcranial magnetic stimulation: report and suggested guidelines from the International Workshop on the Safety of Repetitive Transcranial Magnetic Stimulation, Jun. 5-7, 1996" Electroencephalography and Clinical Neurophysiology/Evoked Potentials Section. Jan. 1, 1998;108(1):1-6.
Zusman M. "Forebrain-mediated sensitization of central pain pathways: 'non-specific' pain and a new image for MT" Manual therapy. May 1, 2002;7(2):80-8.
Brignani, D., Manganotti, P., Rossini, P. M., & Miniussi, C. (2008). Modulation of cortical oscillatory activity during transcranial magnetic stimulation. Human brain mapping, 29(5), 603-612.
International Search report for PCT/IL2015/050774 dated Feb. 4, 2016.
International Search report for PCT/IL2016/050123 dated Aug. 11, 2016.
International Search Report for PCT Application PCT/IL2017/050160 dated Jun. 4, 2017.
International Search Report for PCT Application PCT/IL2015/050720 dated Jan. 21, 2016.
Taylor, P. C., Nobre, A. C., & Rushworth, M. F. (2006). FEF TMS affects visual cortical activity. Cerebral cortex, 17(2), 391-399.

* cited by examiner

EARLY DIAGNOSIS AND TREATMENT OF ALZHEIMER DISEASE AND MILD COGNITIVE IMPAIRMENT

TECHNICAL FIELD

The present disclosure generally relates to the field of neural functionality assessment, diagnosis and treatment of neurodegenerative conditions.

BACKGROUND

Diagnosing neurological conditions accurately and at an early stage is of cardinal importance for the effectiveness of treatments that may be used for treating and/or managing the condition. As in many other medical conditions, it is not always possible to easily detect the conditions at an early stage, and the detection commonly happens when conforming symptoms appear. Waiting until noticeable/perceptible symptoms are detected may provide a high accuracy for diagnostics of a condition, alas, it may also indicate that the condition is in a late stage.

Especially in Neurodegenerative conditions, such as Alzheimer's disease, symptoms become noticeable when a degeneration is already advancing, and the treatment, and sometimes even management, of the condition may be ineffective at such a stage.

There is thus a need in the art for methods, devices and systems for facilitating a detection of neurodegenerative conditions at an early-stage.

SUMMARY

The following embodiments and aspects thereof are described and illustrated in conjunction with systems, tools and methods, which are meant to be exemplary and illustrative, not limiting in scope. In various embodiments, one or more of the above-described problems have been reduced or eliminated, while other embodiments are directed to other advantages or improvements.

According to some embodiments, there are provided herein devices, systems and methods for detecting neurodegenerative conditions by stimulating predetermined brain regions of a subject, and measuring a neural activity response to the stimulation, and assessing the plasticity of the neurons/neural-networks (neuroplasticity) in the predetermined brain regions based on the characteristics of the neural activity response to the stimulation.

According to some embodiments, a treatment may be provided to the subject by providing electrical stimulation sessions targeting the predetermined brain regions, and assessing the effectiveness of the treatment by evaluating the plasticity of the neurons/neural-networks by measuring the neural activity response to neural stimulation.

According to some embodiments, characteristics and parameters of the electrical stimulation sessions may be changed and adapted based on the assessed effectiveness of previous sessions.

According to some embodiments, there is provided a method for assessing and treating a cognitive impairment condition of a subject, the method including inducing an examinatorial/diagnostic stimulation to a predetermined brain region of the subject, measuring a neural activity response to the examinatorial stimulation, evaluating a neuroplasticity of neural-structures in the predetermined brain regions based on the neural activity response to the examinatorial stimulation, assessing a cognitive impairment condition of the subject based on the evaluated neuroplasticity, and inducing a treatment stimulation to the predetermined brain region based on the evaluated neuroplasticity of the neural structures in the predetermined brain region to treat the assessed cognitive impairment.

According to some embodiments, the cognitive impairment condition includes Mild Cognitive Impairment (MCI). According to some embodiments, the cognitive impairment condition includes a neurodegenerative condition. According to some embodiments, the cognitive impairment condition includes Alzheimer's disease. According to some embodiments, the predetermined brain region is selected from a group including: entorhinal cortex, perirhinal cortex, prefrontal cortex, inferior temporal cortex, Para hippocampal entorhinal cortex, prefrontal cortex, posterior cingulate and retrosplenial cortex. According to some embodiments, inducing an examinatorial stimulation to a predetermined brain region of the subject includes utilizing transcranial magnetic stimulation (TMS).

According to some embodiments, inducing an examinatorial stimulation to a predetermined brain region of the subject includes provided the subject with a cognitive/behavioral task configured to induce stimulation to the predetermined brain region. According to some embodiments, measuring a neural activity response to the examinatorial stimulation includes obtaining electroencephalogram (EEG) measurements indicative of a neural activity in the brain of the user during and/or after inducing the examinatorial stimulation.

According to some embodiments, inducing a treatment stimulation to the predetermined brain region includes electric brain stimulation. According to some embodiments, the electric brain stimulation includes placing a first electrode and a second electrode on the subject, such that an electric signal passing through the user via the first electrode and the second electrode reaches a predetermined brain region.

According to some embodiments, the method further including evaluating specific brain areas for plasticity changes by dipole fitting the EEG measurements and performing a source modeling for detecting the location (source localized areas) of the specific areas and providing treatment stimulation to the source localized areas. According to some embodiments, the electric brain stimulation includes transcranial direct current stimulation (tDCS). According to some embodiments, the electric brain stimulation includes transcranial alternating current stimulation (tACS).

According to some embodiments, inducing a treatment stimulation to the predetermined brain region includes providing the subject with audial and/or visual stimulation. According to some embodiments, the audial and/or visual stimulation includes a virtual reality (VR) session configured to stimulate neural activity of the predetermined brain region.

According to some embodiments, the method further includes inducing a post-treatment examinatorial stimulation to the predetermined brain region of the subject, measuring a neural activity response to the post-treatment examinatorial stimulation, evaluating a post-treatment neuroplasticity of neural-structures and functions in the predetermined brain regions based on the neural activity response to the post-treatment examinatorial stimulation, and inducing a treatment stimulation to the predetermined brain region based on the evaluated post-treatment neuroplasticity of the neural structures in the predetermined brain region.

According to some embodiments, there is provided a system for assessing and treating a cognitive impairment condition of a subject, the system including a directed inspective stimulation unit, configured to induce an examinatorial stimulation to a predetermined brain region of the subject, a brain activity sensor, configured to measure a neural activity response to the examinatorial stimulation induced by the directed brain stimulation unit, a processing circuitry in communication with the brain activity sensor, the processing circuitry is configured to evaluate a neuroplasticity of neural-structures in the predetermined brain region based on the neural activity response to the examinatorial stimulation, and a directed treatment stimulation unit, configured to induce a treatment stimulation to the predetermined brain region based on the evaluated neuroplasticity of the neural structures in the predetermined brain region.

According to some embodiments, the directed inspective stimulation unit and the directed treatment stimulation unit are directed brain stimulation operable in at least a first mode of operation and a second mode of operation, such that at the first mode of operation the directed brain stimulation is configured to induce an examinatorial stimulation to a predetermined brain region of the subject, and at the first mode of operation the directed brain stimulation is configured to induce a treatment stimulation to the predetermined brain region based on the evaluated neuroplasticity of the neural structures in the predetermined brain region.

According to some embodiments, the directed inspective stimulation unit includes a transcranial magnetic stimulation (TMS) unit. According to some embodiments, the brain activity sensor includes an electroencephalography (EEG) device. According to some embodiments, the processing circuitry is configured to obtain an EEG signal from the EEG device and evaluate a neuroplasticity of neural-structures in the predetermined brain region by detecting epileptiform like discharges activity. According to some embodiments, the directed treatment stimulation unit includes a tDCS device configured to induce a treatment stimulation to the predetermined brain region by driving a direct current signal through the predetermined brain region using at least two electrodes configured to be positioned on the subject. According to some embodiments, the directed treatment stimulation unit includes a tACS device configured to induce a treatment stimulation to the predetermined brain region by driving an alternating current signal through the predetermined brain region using at least two electrodes configured to be positioned on the subject.

Certain embodiments of the present disclosure may include some, all, or none of the above advantages. One or more technical advantages may be readily apparent to those skilled in the art from the figures, descriptions and claims included herein. Moreover, while specific advantages have been enumerated above, various embodiments may include all, some or none of the enumerated advantages.

In addition to the exemplary aspects and embodiments described above, further aspects and embodiments will become apparent by reference to the figures and by study of the following detailed descriptions.

BRIEF DESCRIPTION OF THE DRAWINGS

Examples illustrative of embodiments are described below with reference to figures attached hereto. In the figures, identical structures, elements or parts that appear in more than one figure are generally labeled with a same numeral in all the figures in which they appear. Alternatively, elements or parts that appear in more than one figure may be labeled with different numerals in the different figures in which they appear. Dimensions of components and features shown in the figures are generally chosen for convenience and clarity of presentation and are not necessarily shown in scale. The figures are listed below.

DETAILED DESCRIPTION

In the following description, various aspects of the disclosure will be described. For the purpose of explanation, specific configurations and details are set forth in order to provide a thorough understanding of the different aspects of the disclosure. However, it will also be apparent to one skilled in the art that the disclosure may be practiced without specific details being presented herein. Furthermore, well-known features may be omitted or simplified in order not to obscure the disclosure.

Alzheimer's disease and mild cognitive impairment have been found to be associated with affecting the brain structure and function, which are expressed in abnormal anatomical and functional connectivity in various brain regions/areas related to memory. These changes in the brain are explained by a neurological/neuro-structural property called neuroplasticity.

Neuroplasticity is manifested in two directions of neural behavior: potentiation, which is when a neural response is increased over time (training) by parts producing strengthening of neuronal connection, or depression, which is when a neural response is decreased over time by parts producing weakening of neuronal connections.

Neuroplasticity can be expressed in both synaptic-neuroplasticity and structural neuroplasticity, and in both, the constructive and destructive directions: synaptic potentiation, synaptic depression, structural potentiation and structural depression.

In synaptic potentiation, the activity of the synapse is increased such that for an action potential, more neurotransmitters are released from the axon terminal into the synapses, or the change may occur in the post synaptic membrane in that the number of neuro-transmitter receptors may increase, or changes to the types of the neurotransmitter receptors, or change in the responses that occur in the second messenger such that the sensitivity to neurotransmitters increases and an increased response per action potential is observed.

On the other hand, synaptic depression can be manifested by a decrease in the neurotransmitter release per action potential, or the number of the receptors is decreased and/or the type of the receptors is changed or changes to second messengers and a decreased response is observed per action potential.

In structural potentiation, the amount, length and strength of dendritic branches and amount and structure of axon terminal forming synapses increases, and the connection between the neurons becomes stronger.

In structural depression, the amount, length and strength of dendritic branches and amount and structure of axon terminal forming synapses increases, and the connection between neurons becomes weaker.

In a normal brain, neuroplasticity comes into effect in that activating a link/connection between neurons commonly promotes potentiation, and the more a connection between neurons is activated, the more the link becomes stronger. On the other hand, not utilizing a link between neurons commonly results in a weakening of the link between the neurons.

In people suffering from Alzheimer's disease or MCI the neural structure and the behavior of the neural activity in some brain regions is affected, and there is a high correlation with altered neuroplasticity in certain brain regions. Therefore, according to some embodiments, Alzheimer's disease and/or MCI may be diagnosed by measuring the neuroplasticity of certain brain regions such as, and not limited to, entorhinal cortex, prefrontal cortex, posterior cingulate, hippocampus, and retrosplenial cortex.

According to some embodiments, the neuroplasticity of the neuro structures in the specific brain regions may be evaluated by providing stimulation to the specific brain regions, and neuroplasticity in a fundamental characteristic of neuronal network at specific brain regions, assessment of personal properties of neuroplasticity provides a tool for evaluating changes in normal brain activity and diagnosis of Alzheimer's disease and its precursor, mild cognitive impairment. Early detection of neuroplasticity changes is critical for treatment of neurodegenerative related brain disorders, which, when diagnosed early, may prevent or delay deterioration by preserving neuroplasticity. According to some embodiments, a healthy neuroplasticity may be indicated by a change in the neural activity response over stimulations.

As used herein, the term "early detection" of the cognitive condition may refer to a detection of the condition even before associated symptoms are apparent.

According to some embodiments, after evaluating the neuroplasticity of the neuro structures in the targeted brain region(s), a stimulation treatment to the brain region(s) may be provided. Such a stimulation treatment may enhance the neuroplasticity of the neuro-structure, thereby providing a treatment to the Alzheimer's disease and/or MCI and/or other neurodegenerative disorders.

According to some embodiments, the stimulation is an electric stimulation. According to some embodiments, the stimulation is an electrically induced electric stimulation. According to some embodiments, the stimulation is a magnetically induced electric stimulation. According to some embodiments, the stimulation is a Transcranial-Magnetic-stimulation.

According to some embodiments, the stimulation includes inducing a magnetic flux/field to the brain or portions thereof. According to some embodiments, the magnetic stimulation may include a Transcranial-Magnetic-stimulation (TMS). According to some embodiments, the stimulation may include multiple TMS magnetic pulses at determined intensities. According to some embodiments, the TMS intensity may refer to the flux of the induced magnetic field. According to some embodiments, the TMS intensity may be measured/presented in Tesla units. According to some embodiments, the TMS intensity may be measured/presented as a percentage of a reference value.

According to some embodiments, measuring the reactive activity may be facilitated by measuring an electric activity of neural structures in the brain in response to an electric/electromagnetic stimulation. According to some embodiments, measuring the reactive activity may be facilitated by utilizing at least one electrode, configured to measure variations of electric fields indicative of an activity of specific neural networks in the brain. According to some embodiments, measuring the reactive activity may be facilitated by utilizing an EEG device/system. According to some embodiments, measuring the reactive activity may be facilitated by measuring an electric activity of neural structures in the brain in response to a provided cognitive task, auditory stimuli, visual stimuli, electric stimuli, electromagnetic stimuli or any combination thereof.

Figure 1:
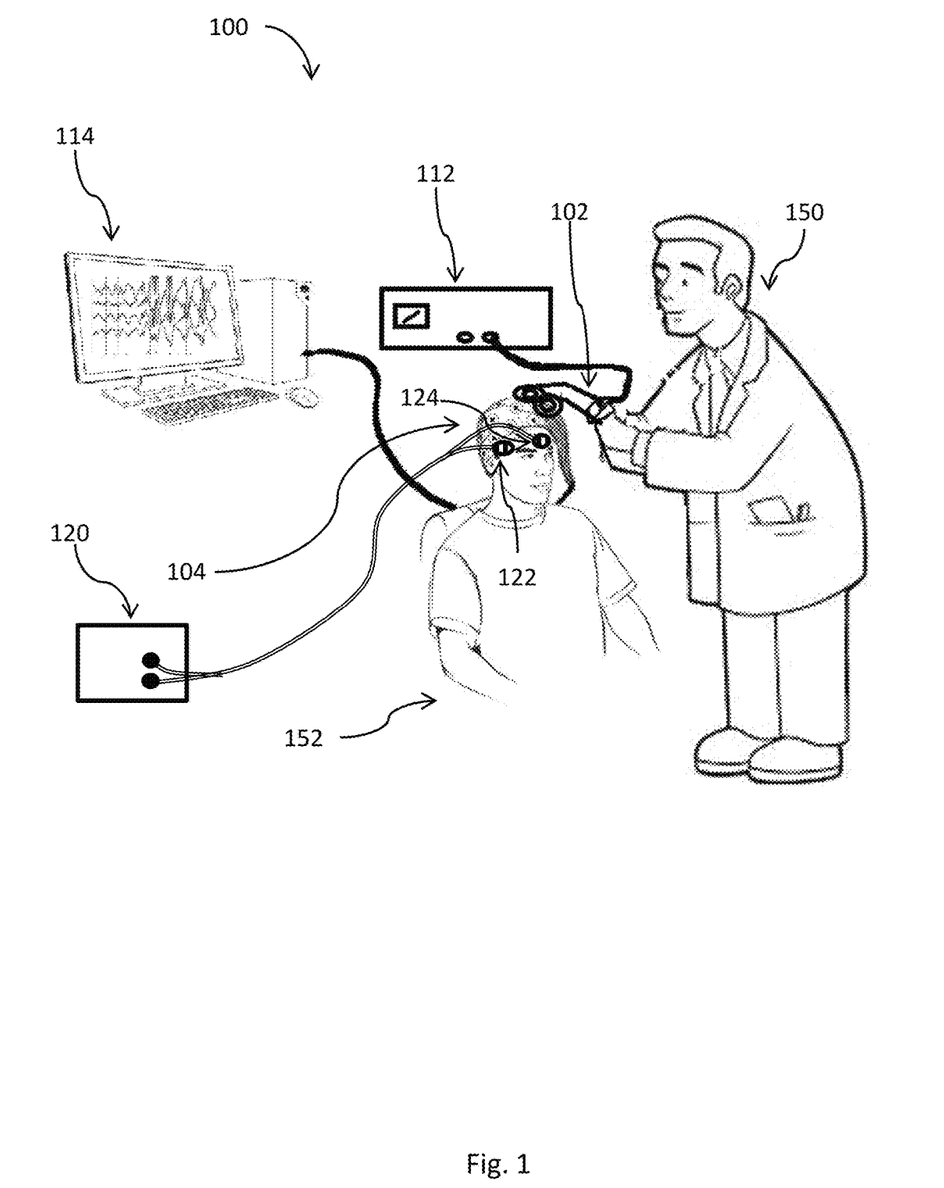
FIG. 1 schematically illustrates a setting of diagnosing and treating a cognitive impairment condition, according to some embodiments.

Reference is now made to FIG. 1, which schematically illustrates a setting 100 of diagnosing and treating a cognitive impairment condition of a subject 152 by a care provider 150, according to some embodiments. As illustrated, care provider 150 places a diagnosis stimulating device, such as but not restricted to TMS-inducer 102, at a certain position on/near the head of subject 152 for inducing stimulation to a target brain region thereof. TMS-inducer 102 is provided with control signals and electric energy from a controller, such as a TMS-controller 112. TMS-controller 112 is configurable for enabling a controllable stimulation by TMS-inducer 112. According to some embodiments, a controllable stimulation may include control over the intensity, duration, frequency, flux and/or other stimulation-related parameters and patterns of stimulation.

At least some brain activity sensors, such as EEG-electrodes 104, are placed on the head of subject 152, and configured to measure neural activity of the brain of subject 152 or defined areas thereof for assessing a neural activity response to the diagnostic stimulation. According to some embodiments, EEG-electrodes 104 are in communicational link with an analyzer/controller, such as an EEG-analyzer 114, configured to obtain EEG signals from EEG-electrodes 104.

According to some embodiments, EEG-analyzer 114, or other processing circuitry (such as remote servers, a cloud computing service, a local computer, distributed computers, and the like), is configured to analyze the obtained EEG signals and detect reactive activity associated with induced electrical stimulation, such as TMS diagnostic stimulations induced by TMS-inducer 102. According to some embodiments, EEG-analyzer 114 is configured to facilitate evaluation of neuroplasticity of the targeted brain regions of subject 152 (or neural structures thereof) by measuring the intensities of the reactive activity, for example by comparing the intensities with model/reference activities expected assuming various conditions and/or lack thereof. According to some embodiments, EEG-analyzer 114 is configured to detect neuroplasticity of the targeted brain regions of subject 152 (or neural structures thereof) by measuring the intensities of the reactive activity and comparing the ratios between various pairs therefrom, and comparing the intensities with model/reference activities expected assuming various conditions and/or lack thereof.

According to some embodiments, EEG-analyzer 114 is configured to analyze the EEG signals relying on their amplitudes, slopes, frequencies, delays, area under curve and the like. According to some embodiments, EEG-analyzer 114 is configured to perform a frequency analysis of the EEG signals. According to some embodiments, EEG-analyzer 114 is configured to perform noise reduction filtration on the EEG-signals. According to some embodiments, EEG-analyzer 114 is configured to perform noise cancellation filtration on the EEG-signals. According to some embodiments, EEG-analyzer 114 is configured to perform a temporal analysis of the EEG signals.

According to some embodiments, a treatment stimulation mechanism is provided, such as transcranial current stimulation (tCS) device 120, which is configured to provide treatment of brain stimulation to the target brain regions by sending an electric signal through a cathode 122 and an anode 124 placed on subject 152 at desired positions for inducing stimulation to the target brain regions.

According to some embodiments, a Neuronal stimulator, such as, TMS-unit 102 is configured to induce multiple stimuli pulses. According to some embodiments, the multiple stimuli pulses are substantively equal in intensity. According to some embodiments, the multiple stimuli pulses are substantively equal in duration. According to some embodiments, the multiple stimuli pulses are substantively similar in slopes. According to some embodiments, the multiple stimuli differ in intensity, duration, and/or slopes.

According to some embodiments, the treatment stimulation mechanism and/or the diagnostic stimulation mechanism may include other brain stimulation means, such as, but not limited to, auditory stimulation, visual stimulation or others or any combination thereof.

Other stimulation mechanisms may include cognitive tasks utilizing virtual reality environment or other method to explore spatial memory, cognitive reaction and working memory. MCI is characterized by deterioration in performance during these tasks Decrease in plasticity in brain regions such as but not restricted to entorhinal cortex, perirhinal cortex, prefrontal cortex, inferior temporal cortex, Para hippocampal, areas is associated with MCI, which may be evaluated by combining TMS with EEG. In addition, epileptoform like activity in temporal areas may also indicate MCI progression.

Treatment stimulation may include for example, but not restricted to, a minimal invasive subcutaneous implant of tCS for direct/alternate cathodal or anodal stimulation in one of the brain regions associated with decrease in neuroplasticity as mentioned above for the treatment of Alzheimer's disease or its precursor MCI, or early detection. Stimulation properties may change according to evaluated neuroplasticity changes in relevant monitored specific areas.

Treatment stimulation may include for example non-invasive tDCS and/or tACS treatment in one of the brain regions associated with decrease in neuroplasticity as mentioned above for the treatment of Alzheimer's disease or its precursor MCI, or early detection. Stimulation properties may change according to evaluated neuroplasticity changes in relevant monitored specific areas.

According to some embodiments, the location of the treatment stimulation electrodes may be determined by evaluating specific brain areas for plasticity changes by dipole fitting the EEG measurements and performing a source modeling for detecting the location (source localized areas) of the specific areas and providing treatment stimulation to the source localized areas. According to some embodiments, the localization may be achieved by fitting electrical field distribution model from the EEG to MRI scans, and source localization of EEG data.

According to some embodiments, the devices, systems and/or methods may be used for assessing the progress and/or state of a diagnosed subject. According to some embodiments, the devices, systems and/or methods may be used for measuring a stage/severity of a disorder or condition. According to some embodiments, the devices, systems and/or methods may be used for detecting and/or assessing neural network abnormalities.

According to some embodiments, evaluating the neuroplasticity of target brain regions may be done by providing stimulation to the target brain region and measuring the reactive neural activity of that region. According to some embodiments, evaluating the neuroplasticity of target brain regions may be done by iteratively providing stimulation to the target brain region, measuring the reactive neural activity of that region, and assessing the changes in reactive neural activity between different iterations.

Figure 2A:
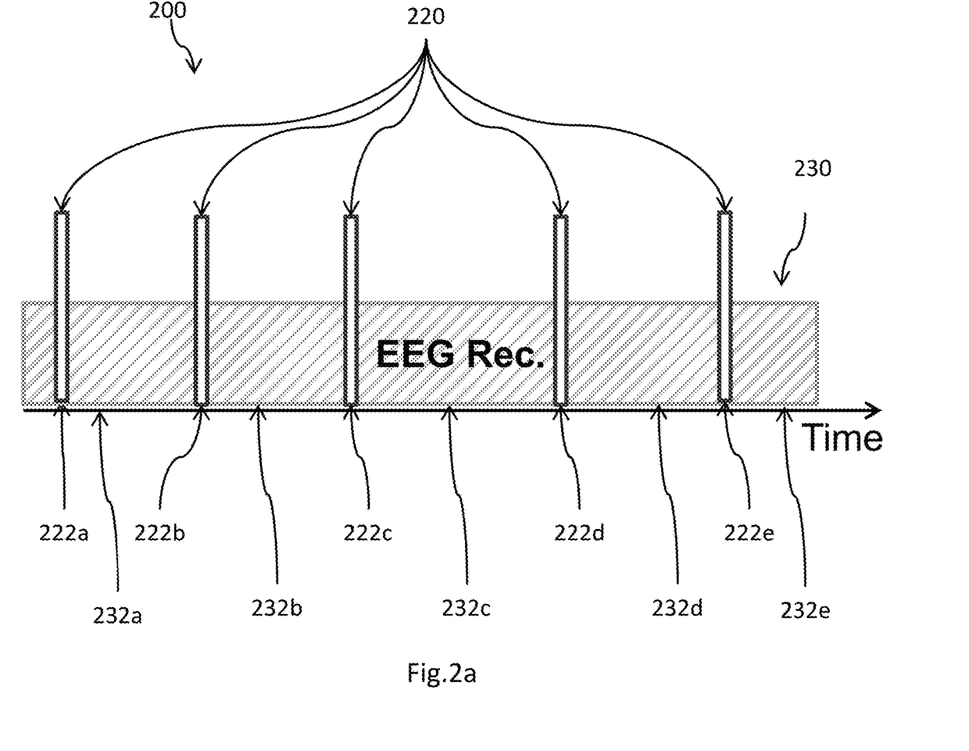
FIG. 2a schematically illustrates a repetitive diagnosis process, according to some embodiments.

Reference is now made to FIG. 2a, which schematically illustrates a repetitive diagnosis process 200, according to some embodiments. According to some embodiments, diagnosis process 200 may include multiple diagnostic stimulation events, such as diagnostic stimuli pulses 220, configured to induce stimulation, evoked by a diagnostic stimulation device, such as TMS, at determined times and intensities. According to some embodiments, diagnosis process 200 further includes sensing brain activity of the user, for example using EEG-monitoring 230 for measuring the response activity to stimuli pulses 220. According to some embodiments, EEG-monitoring 230 may be continuous throughout the period of stimulation pulses 220. According to some embodiments, EEG monitoring 230 may be intermittent.

According to some embodiments, stimuli pulses 220 comprise a first stimulus pulse 222a followed by a first pulse delay interval 232a, a second stimulus pulse 222b followed by a second pulse delay interval 232b, a third stimulus pulse 222c followed by a third pulse delay interval 232c, a fourth stimulus pulse 222d followed by a fourth pulse delay interval 232d and a fifth stimulus pulse 222e followed by a fifth pulse delay interval 232e.

According to some embodiments, pulse delay intervals 232a, 232b, 232c, 232d, 232e are configured to enable distinguishing between EEG recording/monitoring of reaction activity associated with each of stimulus pulses 222a, 222b, 222c, 222d, 222e.

According to some embodiments, stimulus pulses 222a, 222b, 222c, 222d, 222e may be substantively equal in intensity. According to some embodiments, stimulus pulses 222a, 222b, 222c, 222d, 222e may vary in intensity.

According to some embodiments, stimulus pulses 222a, 222b, 222c, 222d, 222e may be substantively equal in duration. According to some embodiments, stimulus pulses 222a, 222b, 222c, 222d, 222e may vary in duration.

According to some embodiments, pulse delay intervals 232a, 232b, 232c, 232d, 232e may be substantively equal in duration. According to some embodiments, pulse delay intervals 232a, 232b, 232c, 232d, 232e may vary in duration.

Figure 2B:
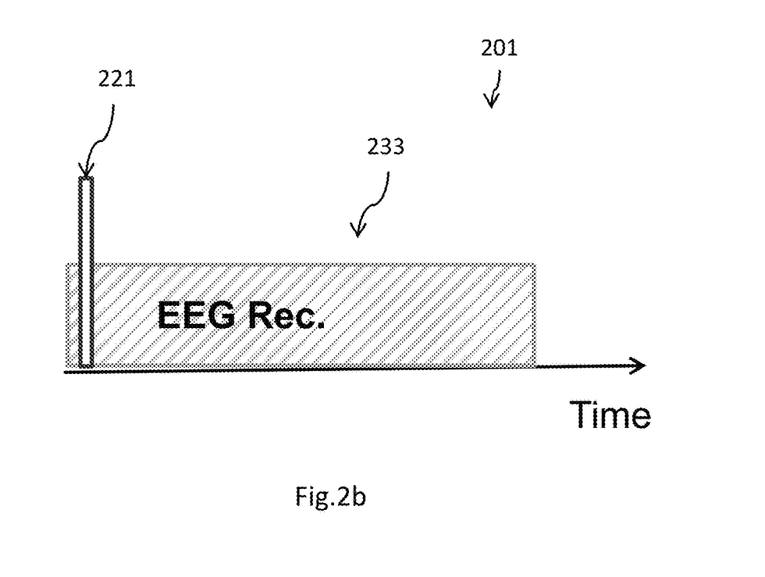
FIG. 2b schematically illustrates a singular diagnosis process, according to some embodiments.

Reference is now made to FIG. 2b, which schematically illustrates a singular diagnosis process 201, according to some embodiments. According to some embodiments, an evaluation of the neuroplasticity of the target brain region may be enabled by a non-iterative stimulation event 221 and monitoring of a neural reactive response thereto, for example by EEG-monitoring 233.

According to some embodiments, the duration of a pulse is in the range of 0.5 ms to 2 ms. According to some embodiments, the duration of a pulse is in the range of 1 ms to 1.5 ms. According to some embodiments, the duration of a pulse is approximately 1 ms.

According to some embodiments, the delay intervals are in the range of 100 ms to 2 s. According to some embodiments, the delay intervals are in the range of 250 ms to 1 s. According to some embodiments, the delay intervals are approximately of 500 ms. According to some embodiments, the pulse frequency within a burst is in the range of 0.1 Hz to 10 Hz. According to some embodiments, the pulse frequency within a burst is in the range of 1 Hz to 5 Hz. According to some embodiments, the pulse frequency is approximately 2 Hz.

According to some embodiments, the reaction activity of the neural network in the brain is expected to vary between consecutive stimulus pulses. This may be attributed to the neuro-structural characters of plasticity and excitability. As a result, the reaction activity associated with the second stimuli pulse may be considerably higher than the reaction activity associated with the first stimuli pulse. Additionally, in later stimulus pulses, a gradual decrease in the reaction activity may be expected.

The amount/ratio of increased and/or decreased activity may be indicative of the characteristics of the neuronal network (neural structures), such as plasticity and excitation and inhibition. Consequently, one may detect irregularities in these characteristics and associate them with various conditions that may lead to changes in these characteristics.

According to some embodiments, a stimulation burst may include 1 or more stimuli pulses. According to some embodiments, a stimulation burst may include 2 or more stimuli pulses. According to some embodiments, a stimulation burst may include 3 or more stimuli pulses. According to some embodiments, a stimulation burst may include 4 or more stimuli pulses. According to some embodiments, a stimulation burst may include 5 or more stimuli pulses. According to some embodiments, a stimulation burst may include 2 to 10 stimuli pulses. According to some embodiments, a stimulation burst may include 10 or more stimuli pulses.

According to some embodiments, a session of diagnosis and treatment is provided by performing diagnosis (assessment of neuroplasticity) and providing treatment stimulation. According to some embodiments, an efficiency of a treatment may be evaluated by performing another diagnosis (assessment of neuroplasticity), and based on the effectiveness assessment, another treatment session may be provided. According to some embodiments, parameters and characteristics of the second and following treatment sessions may be determined based on the assessed effectiveness of the first treatment.

Figure 3:
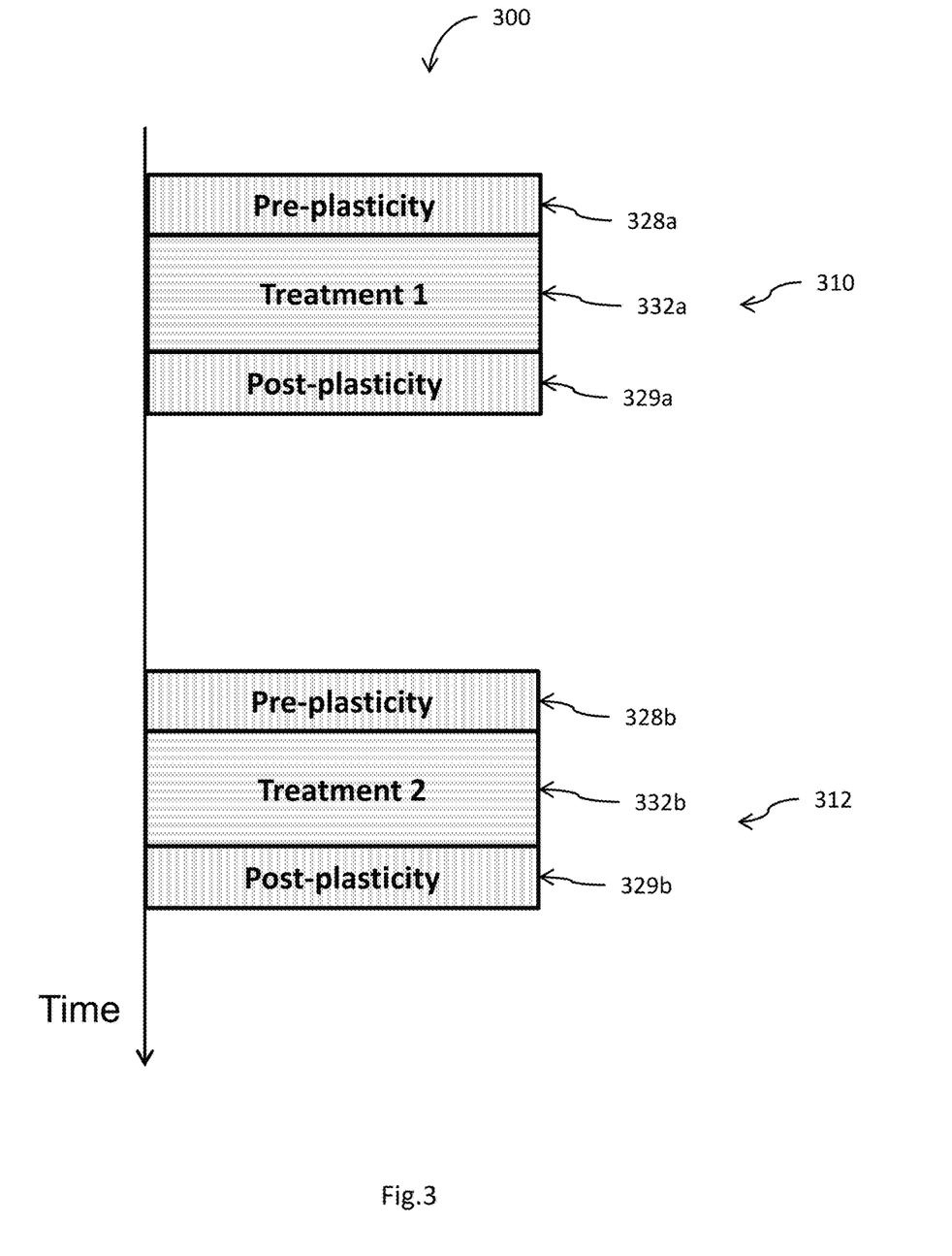
FIG. 3 schematically illustrates a session of iterative diagnosis and treatment, according to some embodiments.

Reference is now made to FIG. 3, which schematically illustrates a session 300 of evaluation and treatment, according to some embodiments. According to some embodiments, the subject may undergo a first round of treatment 310, where the pre-treatment plasticity of certain brain regions may be evaluated 328a for diagnosing the condition and determining a treatment, and a treatment stimulation 332a may be provided. Afterwards, a post treatment plasticity is evaluated 329a to assess the efficacy of the first treatment.

According to some embodiments, the subject may then, after a period of time, undergo a second round of treatment 312, in the plasticity of certain brain regions may be evaluated 328b for determining a treatment and progress of the condition compared to first round of treatment 310, and a second treatment stimulation 332b may be provided. Afterwards, a post treatment plasticity is evaluated 329b to assess the efficacy of the second treatment.

According to some embodiments, a stimulation session may include 2 or more diagnosis periods. According to some embodiments, a stimulation session may include 3 or more diagnosis periods. According to some embodiments, a stimulation session may include 5 to 10 diagnosis periods. According to some embodiments, a stimulation session may include 10 or more diagnosis periods.

According to some embodiments, a diagnosis period may be essentially as described in FIG. 2a or FIG. 2b.

According to some embodiments, some parameters, characteristics and/or features that may be considered for assessing the neuroplasticity characteristics may include one or more of the following: amplitudes, slopes, frequencies, delays, area under curve and the ratios between. According to some embodiments, these parameters may be in response to stimulation pulses, or in association thereto.

Figure 4:
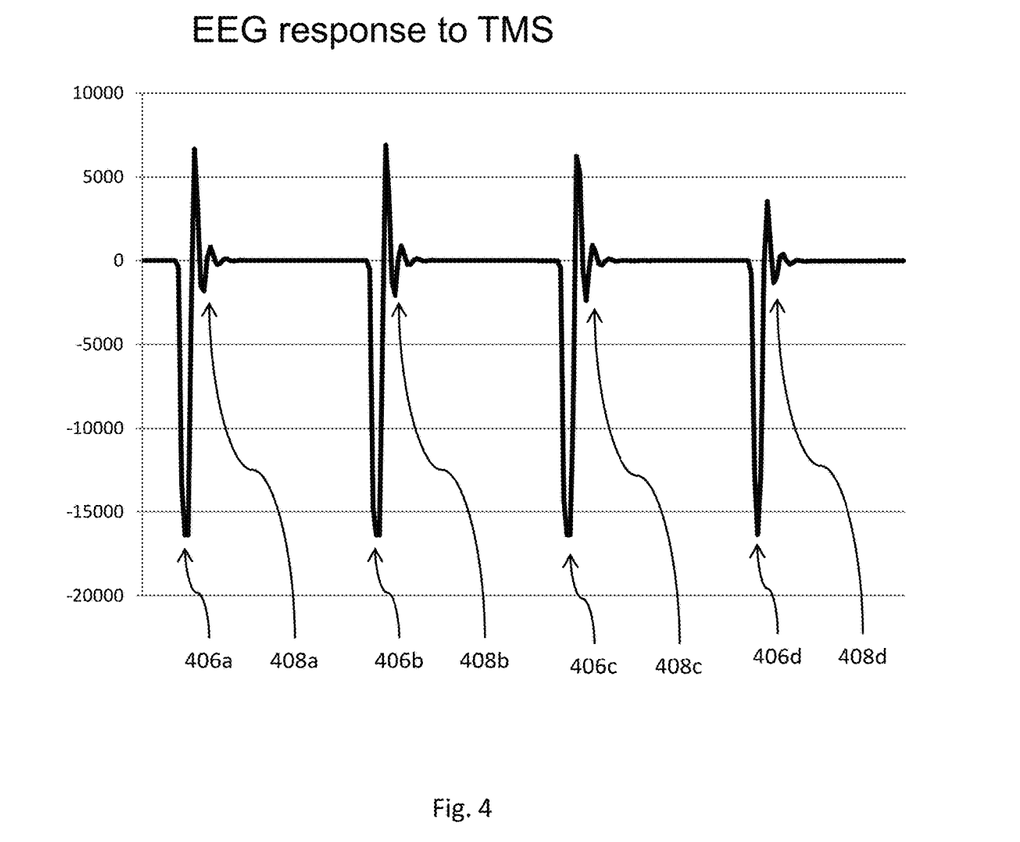
FIG. 4 schematically illustrates an EEG response to a stimulation burst in a healthy brain, according to some embodiments.

Reference is now made to FIG. 4, which schematically illustrates an EEG response activity to a stimulation burst in a normal brain, according to some embodiments. As illustrated, the stimulation burst includes four stimulation pulses, the EEG recording thereof is illustrated in a first pulse recording 406a, a second pulse recording 406b, a third pulse recording 406c and a fourth pulse recording 406d. Following each pulse recording, there is a response recording, namely a first response recording 408a, a second response recording 408b, a third response recording 408c and a fourth response recording 408d. As illustrated, second response recording 408b and third response recording 408c are greater than first response recording 408a, which may be attributed to the excitability or plasticity characteristics of the relevant neural network, while forth response recording 408d is considerably reduced compared to the rest of the responses recorded, which may be attributed to the adaptation characteristics of the relevant neural network.

According to some embodiments, responses that vary from the normal response or a normal response range may indicate various abnormal neural network characteristics.

According to some embodiments, the intensity of pulses is determined as a percentage of a reference value. According to some embodiments, the reference value is determined as a percentage from the personal determined motor-threshold value.

According to some embodiments, a motor threshold is a stimulation intensity at which a motoric reaction may be triggered and/or detected as a consequence thereto.

According to some embodiments, a motor threshold value is established by increasingly incrementing stimulation intensity, until a motoric reaction is detected. According to some embodiments, the motoric threshold may vary from one person to another. According to some embodiments, using a TMS stimulator to induce focal electrical stimulation in the brain, the motor threshold value may be in the range of 1.5 to 2.5 Tesla. According to some embodiments, the motor threshold value may be in the range of 1.7 to 2.3 Tesla. According to some embodiments, the motor threshold value may be in the range of 1.8 to 2.2 Tesla. According to some embodiments, the motor threshold value may be in the range of 1.9 to 2.1 Tesla. According to some embodiments, the motor threshold value may be in the range of 48% to 52% of the maximal TMS device intensity. According to some embodiments, the motor threshold value may be approximately 50% of the maximal TMS device intensity.

Once a motor threshold value is established for a certain person, one may evaluate/calculate an "operational range", which is a range of intensity values in which a reaction activity may be observed and activity corresponds to the intensity of the stimuli. According to some embodiments, the term "operational range" may be interchangeable with the terms "relevant range" or "active range".

According to some embodiments, an "operational range" ranges from 60% to 140% of the motor threshold. According to some embodiments, an "operational range" ranges from 80% to 120% of the motor threshold. According to some embodiments, an "operational range" ranges from 50% to 150% of the motor threshold.

According to some embodiments, the intensity of the stimuli pulses may be a value within the "operational range". According to some embodiments, the intensity of the stimuli pulses may be referred to as an "operational point".

Figure 5:
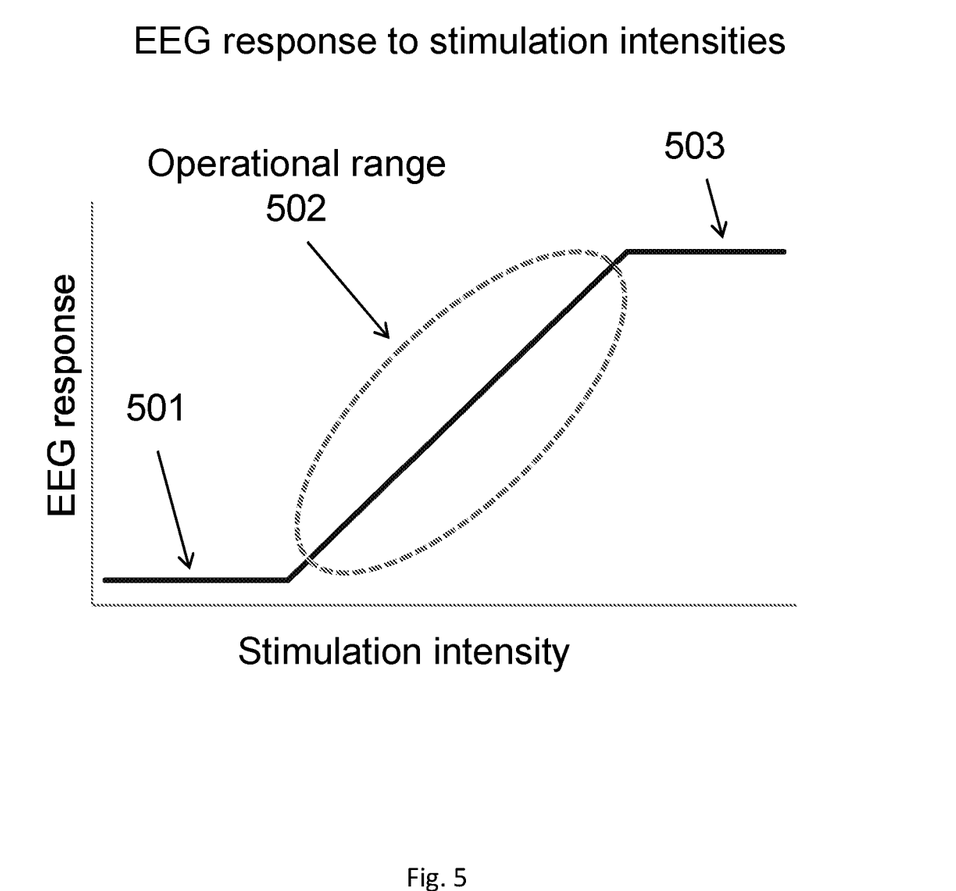
FIG. 5 schematically illustrates a diagnostic stimulation intensity operation range, according to some embodiments.

Reference is now made to FIG. 5, which schematically illustrates a stimulation intensity operational range 502, according to some embodiments. As illustrated, the EEG response to low stimulation intensities is relatively unchanged 501, until the stimulation intensity surpasses a certain value (lower threshold), then the EEG response reacts/increases as the stimulation intensity increases 502, until the stimulation intensity reaches another value (upper threshold) in which the EEG response no longer responds to increases in the stimulation intensity 503.

According to some embodiments, the operational range is a range of intensity values between the lower threshold and the upper threshold.

Figure 6:
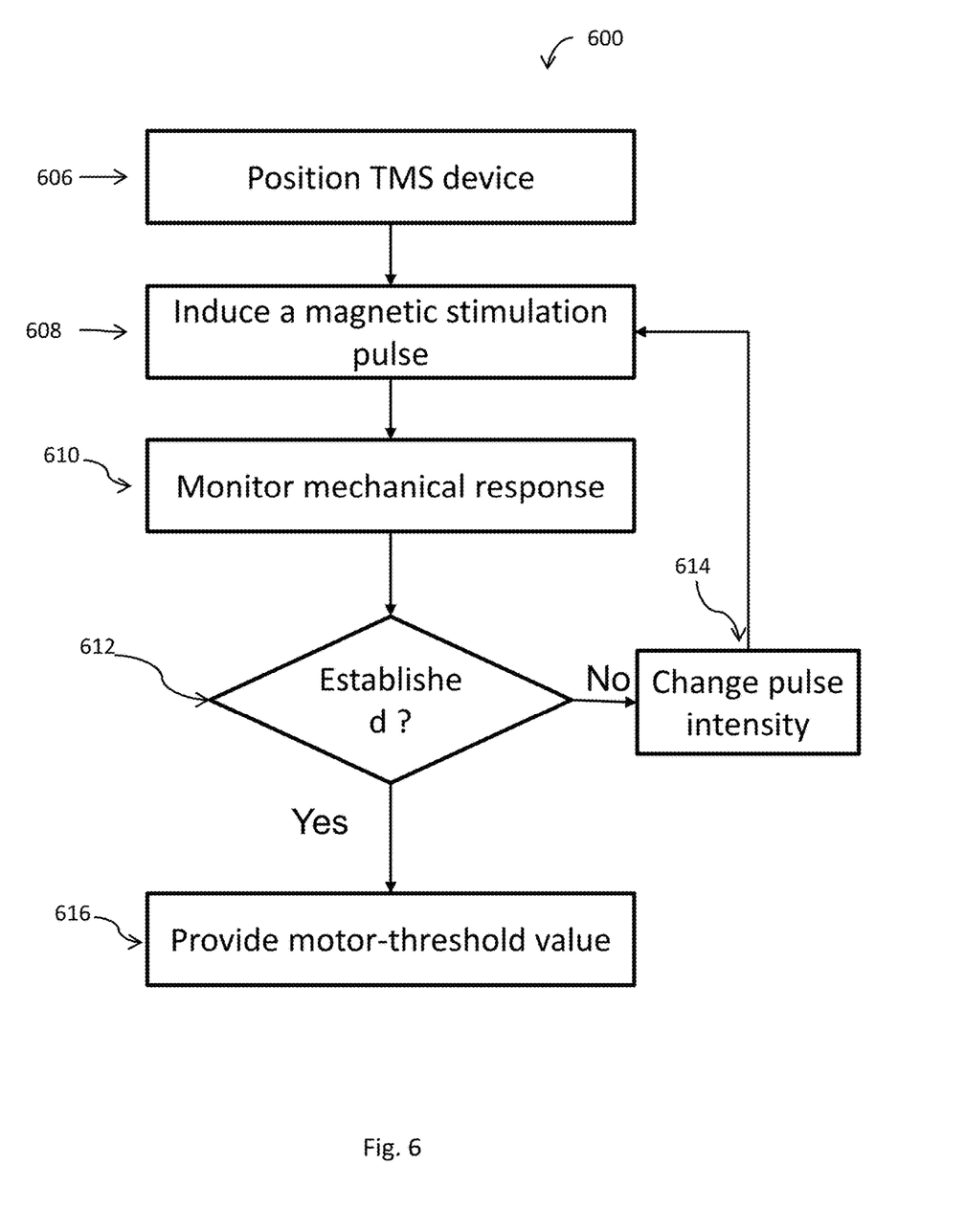
FIG. 6 schematically illustrates a method for establishing a motor threshold value for diagnosis, according to some embodiments.

Reference is now made to FIG. 6, which schematically illustrates a method 600 for establishing a motor threshold value, according to some embodiments. According to some embodiments, the TMS device/unit is positioned (step 606) in a determined position on/near the head of the subject, then a magnetic stimulation pulse is induced (step 608), then the mechanical response is monitored (step 610) for detecting triggered motoric movement. According to some embodiments, if a motoric movement is detected, and a motor threshold established (step 612), the motor threshold value is provided (step 616), otherwise, the pulse intensity is changed (step 614) and we iterate the steps from inducing the magnetic stimulation pulse (step 608).

According to some embodiments, changes to the pulse intensity (step 614) include increasing the pulse intensity.

Figure 7:
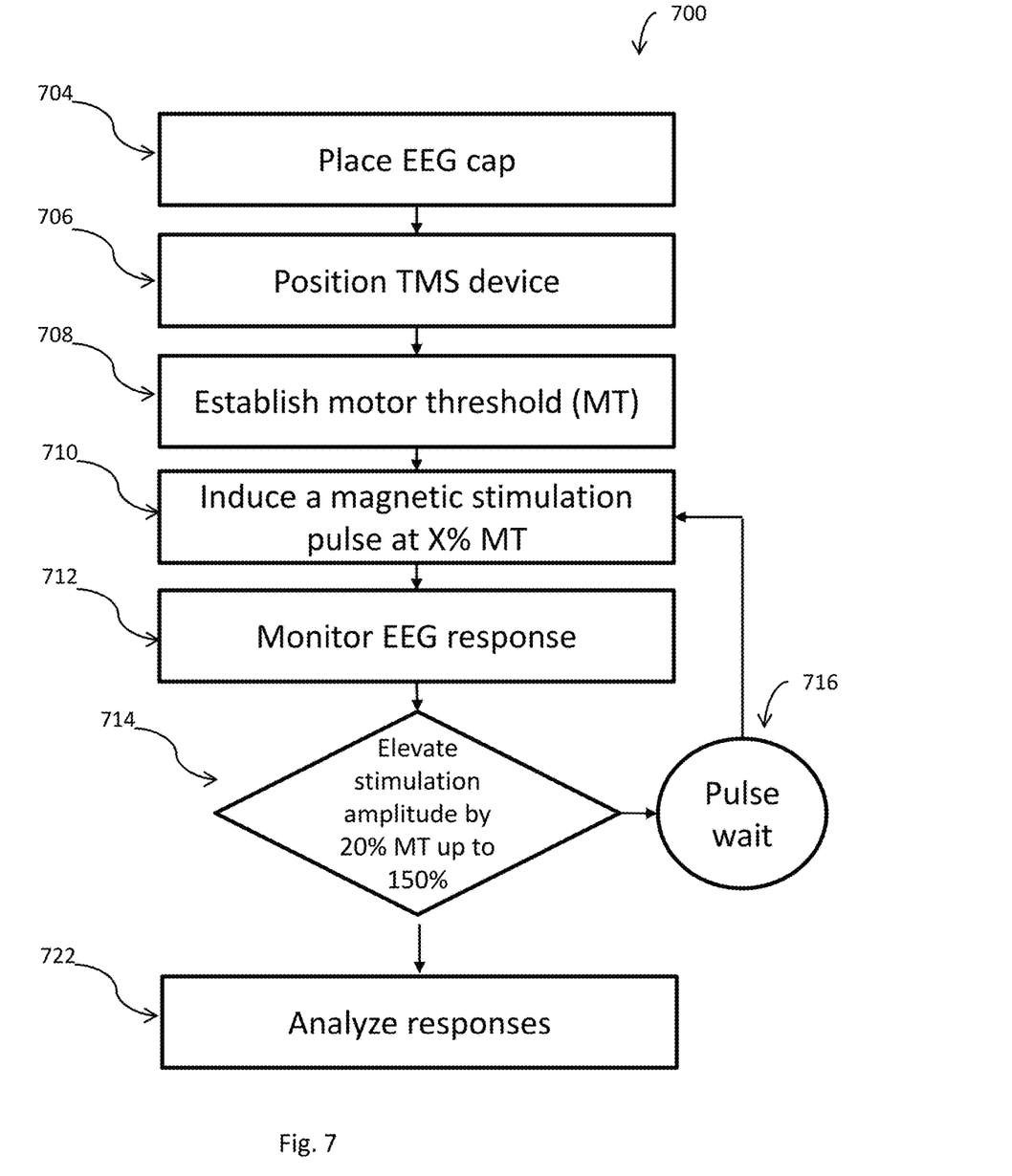
FIG. 7 schematically illustrates a method for providing diagnostic stimulated EEG response bursts, according to some embodiments.

Reference is now made to FIG. 7, which schematically illustrates a method 700 for providing a stimulated EEG response session, according to some embodiments. According to some embodiments, an EEG cap is placed on the head of a subject (step 704), then a TMS device is positioned on/near the head of the subject (step 706), then a motor threshold ("MT") is established (step 708), then a magnetic stimulation pulse is induced (step 710) having an intensity of X % of the established MT. According to some embodiments, the X % is a predetermined percentage of the MT. According to an operational range/value based on the motor threshold, then the EEG response activity is monitored, (step 712), then optionally steps 710 and 712 are repeated as the stimulation amplitude is elevated by a predetermined percentage up to a certain level, for example 20% up to 150%, (step 714) with a "pulse-wait" delay between iterations (step 716), and the response activity is analyzed (step 722).

Figure 8:
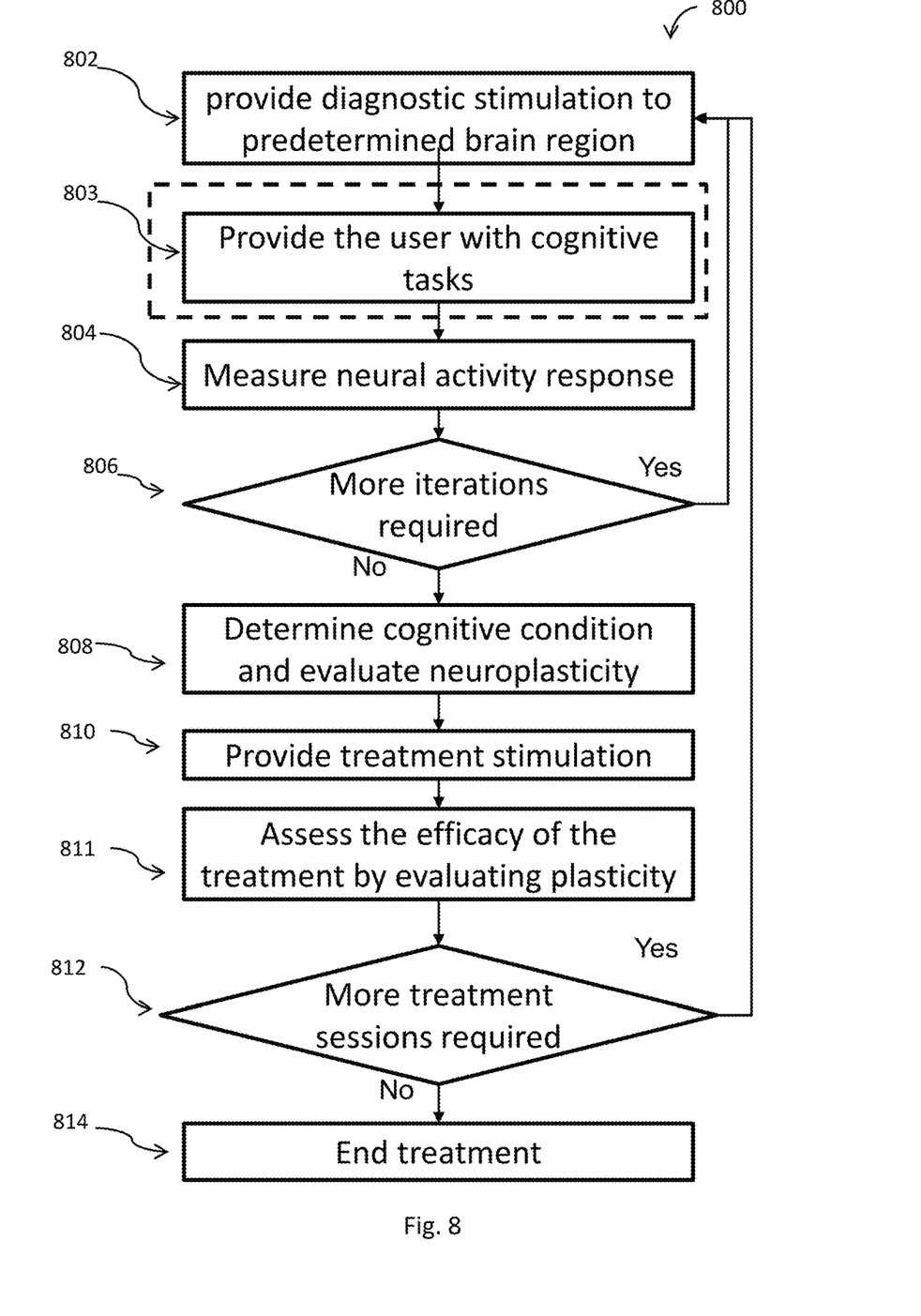
FIG. 8 schematically illustrates a method for iterative diagnosis and treatment, according to some embodiments.

Reference is now made to FIG. 8, which schematically illustrates a method 800 for iterative diagnosis and treatment, according to some embodiments. According to some embodiments, method 800 begins by providing a diagnostic/examinatorial stimulation to a predetermined brain region (step 802), then optionally, the user may be provided with cognitive tasks that are configured to provoke a neural activity of certain brain regions (step 803), then measuring neural activity response to the diagnostic/examinatorial stimulation (step 804), and if more diagnostic iterations are required (step 806), go back to providing a diagnostic/examinatorial stimulation to a predetermined brain region (step 802), otherwise, proceed by evaluating the neuroplasticity and diagnosing the condition (step 808) and provide a treatment stimulation accordingly (step 810). After the treatment the efficacy of the treatment is assessed by evaluating the plasticity of the brain regions (step 811), then if more treatments may be required (step 812), go back to providing a diagnostic/examinatorial stimulation to a predetermined brain region (step 802), otherwise, end treatment session (step 814).

According to some embodiments, a stimulation threshold value is established. According to some embodiments, a stimulation threshold value is a TMS stimulation intensity value, above-which reactive neural activity may be observed/detected.

According to some embodiments, the TMS stimulation intensity is a "supra-threshold", selected to be of a higher intensity than the stimulation threshold.

According to some embodiments, the TMS stimulation intensity is a "sub-threshold", selected to be of a lower intensity than the stimulation threshold.

According to some embodiments, the analysis is conducted after the stimulation session. According to some embodiments, the analysis is conducted during the stimulation session.

According to some embodiments, A and B are predetermined numbers/values.

As used herein, the terms "neuron", "neuro-structure", "neural network" may be interchangeable.

As used herein, the term "TMS" may refer to Transcranial magnetic stimulation, which is a non-invasive method used to stimulate regions of the brain. In TMS, a magnetic field generator, such as a coil or an electromagnet, is placed near/on the head of the subject receiving the stimulation, an electric current is conducted through the coil and a magnetic flux gradient is induced as a result of the change in current through the coil. According to some embodiments, the coil (or electromagnet coil) is connected to a pulse generator, or controller, or stimulator configured to deliver electric current to the coil.

As used herein, the terms "tCS", "tDCS" and "tACS" refer to a brain stimulation technique in whish electric current is driven though the crania of the user to reach and stimulate a desired region, and the electric current is provided to the crania using at least two electrodes placed at defined places such that driving a current signal via the electrodes through the crania may reach the desired brain region.

According to some embodiments, the tACS is performed by inducing an alternating current at a frequency in the range of 1-120 Hz at current density of 5 A/m$^2$ to be matched with a desired oscillatory behavior needed, for example to induce 8-12 Hz activity, a 10 Hz tACS frequency will be administered.

As used herein, the term "EEG" may refer to Electroencephalography, which is typically a non-invasive method for recording electrical activity of the brain along the scalp. An EEG measures voltage fluctuation resulting from ionic current within the neurons/neuro-structures of the brain. According to some embodiments, an EEG may refer to the recording of the brain's spontaneous and/or stimulated electrical activity over a period of time.

As used herein, the term "plasticity" may refer to neuro-plasticity or brain plasticity which may encompass synaptic and/or non-synaptic plasticity, and may refer to changes in neural pathways and synapses and/or structure due to changes in behavior, environment, neural processes, thinking, emotions, injuries and stimulation.

As used herein, the terms "examinatorial" and "diagnostic" stimulation may be interchangeably used and refer to stimulation(s) that are intended to examine a neural behavior and/or diagnose a cognitive condition.

The terminology used herein is for the purpose of describing particular embodiments only and is not intended to be limiting. As used herein, the singular forms "a", "an" and "the" are intended to include the plural forms as well, unless the context clearly indicates otherwise. It will be further understood that the terms "comprises" or "comprising," when used in this specification, specify the presence of stated features, integers, steps, operations, elements, or components, but do not preclude or rule out the presence or addition of one or more other features, integers, steps, operations, elements, components, or groups thereof.

While a number of exemplary aspects and embodiments have been discussed above, those of skill in the art will recognize certain modifications, additions and sub-combinations thereof. It is therefore intended that the following appended claims and claims hereafter introduced be interpreted to include all such modifications, additions and sub-combinations as are within their true spirit and scope.

The invention claimed is:

1. A method for assessing and treating a cognitive impairment condition of a subject, the method comprising:
   inducing examinatorial/diagnostic transcranial magnetic stimulation (TMS) pulses to a predetermined brain region of the subject; wherein the intensity of the TMS pulses is within a range, in which the subject's brain neural activity response is reactive to a change of the TMS pulse intensity;
   measuring a neural activity response to the examinatorial stimulation;
   evaluating a neuroplasticity of neural-structures in the predetermined brain regions based on the neural activity response to the examinatorial stimulation;
   assessing a cognitive impairment condition of the subject based on the evaluated neuroplasticity; and
   inducing a treatment stimulation to the predetermined brain region based on the evaluated neuroplasticity of the neural structures in the predetermined brain region to treat the assessed cognitive impairment.

2. The method of claim 1, wherein the cognitive impairment condition comprises Mild Cognitive Impairment (MCI), a neurodegenerative condition or Alzheimer's disease.

3. The method of claim 1, wherein the predetermined brain region is selected from a group comprising: entorhinal cortex, perirhinal cortex, prefrontal cortex, inferior temporal cortex, Para hippocampal entorhinal cortex, prefrontal cortex, posterior cingulate and retrosplenial cortex.

4. The method of claim 1, wherein the inducing of TMS stimulation to a predetermined brain region of the subject, further comprises providing the subject with a cognitive/behavioral task configured to induce stimulation to the predetermined brain region.

5. The method of claim 1, wherein the measuring comprises obtaining electroencephalogram (EEG) measurements indicative of the neural activity in the brain of the subject, during and/or after inducing the examinatorial stimulation.

6. The method of claim 5, wherein the inducing the treatment stimulation to the predetermined brain region comprises inducing electric brain stimulation.

7. The method of claim 6, wherein the electric brain stimulation comprises transcranial direct current stimulation (tDCS) or transcranial alternating current stimulation (tACS).

8. The method of claim 5, wherein the electric brain stimulation comprises placing a first electrode and a second electrode on the subject, such that an electric signal passing through the subject via the first electrode and the second electrode reaches a predetermined brain region.

9. The method of claim 5, further comprising evaluating specific brain areas for plasticity changes by dipole fitting the EEG measurements and performing a source modeling for detecting the location of the specific areas and providing treatment stimulation to the source localized areas.

10. The method of claim 1, wherein inducing a treatment stimulation to the predetermined brain region comprises providing the subject with audial and/or visual stimulation.

11. The method of claim 10, wherein the audial and/or visual stimulation comprises a virtual reality (VR) session configured to stimulate neural activity of the predetermined brain region.

12. The method of claim 1, further comprising:
   inducing a post-treatment examinatorial stimulation to the predetermined brain region of the subject;
   measuring a neural activity response to the post-treatment examinatorial stimulation;
   evaluating a post-treatment neuroplasticity of neural-structures and functions in the predetermined brain regions based on the neural activity response to the post-treatment examinatorial stimulation; and
   inducing a treatment stimulation to the predetermined brain region based on the evaluated post-treatment neuroplasticity of the neural structures in the predetermined brain region.

13. A system for assessing and treating a cognitive impairment condition of a subject, the system comprising:
   a directed inspective stimulation unit, configured to induce an examinatorial stimulation to a predetermined brain region of the subject; the unit comprises a magnetically induced stimulation device and a controller thereof, configured to provide transcranial magnetic stimulation (TMS) pulses to the region of the brain of the subject, wherein the intensity of the provided TMS pulses is within a range, in which the subject's brain neural activity response is reactive to a change of the TMS pulse intensity;
   a brain activity sensor, configured to measure a neural activity response to the examinatorial stimulation induced by said directed brain stimulation unit;
   a processing circuitry in communication with said brain activity sensor, said processing circuitry is configured to evaluate a neuroplasticity of neural-structures in the predetermined brain region based on the neural activity response to the examinatorial stimulation; and
   a directed treatment stimulation unit, configured to induce a treatment stimulation to the predetermined brain region based on the evaluated neuroplasticity of the neural structures in the predetermined brain region.

14. The system of claim 13, wherein said directed inspective stimulation unit and said directed treatment stimulation unit are directed brain stimulation operable in at least a first mode of operation and a second mode of operation, such that at the first mode of operation said directed brain stimulation is configured to induce an examinatorial stimulation to a predetermined brain region of the subject, and at the first mode of operation said directed brain stimulation is configured to induce a treatment stimulation to the predetermined brain region based on the evaluated neuroplasticity of the neural structures in the predetermined brain region.

15. The system of claim 13, wherein said brain activity sensor comprises an electroencephalography (EEG) device.

16. The system of claim 15, wherein said processing circuitry is configured to obtain an EEG signal from said EEG device and evaluate a neuroplasticity of neural-structures in the predetermined brain region by detecting epileptiform discharges.

17. The system of claim 13, wherein said directed treatment stimulation unit comprises a tDCS device configured to induce a treatment stimulation to the predetermined brain region by driving a direct current signal through the predetermined brain region using at least two electrodes configured to be positioned on the subject.

18. The system of claim 13, wherein said directed treatment stimulation unit comprises a tACS device configured to induce a treatment stimulation to the predetermined brain region by driving an alternating current signal through the predetermined brain region using at least two electrodes configured to be positioned on the subject.

* * * * *